United States Patent
Siochi

(10) Patent No.: US 6,968,035 B2
(45) Date of Patent: Nov. 22, 2005

(54) SYSTEM TO PRESENT FOCUSED RADIATION TREATMENT AREA

(75) Inventor: Ramon Alfredo Carvalho Siochi, Germantown, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 45 days.

(21) Appl. No.: 10/255,856

(22) Filed: Sep. 26, 2002

(65) Prior Publication Data

US 2003/0206612 A1 Nov. 6, 2003

Related U.S. Application Data

(60) Provisional application No. 60/377,352, filed on May 1, 2002.

(51) Int. Cl.[7] ................................................. A61N 5/10
(52) U.S. Cl. ............................ 378/65; 378/62; 378/64; 378/205
(58) Field of Search .............................. 378/51, 53, 54, 378/57, 62, 64, 65, 84, 85, 145, 205, 206, 207

(56) References Cited

U.S. PATENT DOCUMENTS

| | | | |
|---|---|---|---|
| 1,865,441 A | | 7/1932 | Mutscheller |
| 2,557,662 A | | 6/1951 | Kirkpatrick |
| 5,142,559 A | | 8/1992 | Wielopolski et al. |
| 5,604,782 A | | 2/1997 | Cash, Jr. |
| 5,661,773 A | * | 8/1997 | Swerdloff et al. ............ 378/65 |
| 5,761,256 A | * | 6/1998 | Inoue et al. ................. 378/84 |
| 5,870,697 A | * | 2/1999 | Chandler et al. ........... 702/179 |
| 6,094,471 A | * | 7/2000 | Silver et al. ................. 378/84 |
| 6,125,295 A | | 9/2000 | Cash, Jr. et al. |
| 6,195,410 B1 | | 2/2001 | Cash, Jr. |
| 6,359,963 B1 | | 3/2002 | Cash |
| 6,366,801 B1 | | 4/2002 | Cash, Jr. et al. |
| 6,754,304 B1 | * | 6/2004 | Kumakhov .................. 378/45 |
| 6,782,073 B2 | * | 8/2004 | Collins ....................... 378/65 |
| 2001/0043667 A1 | | 11/2001 | Antonell et al. |

FOREIGN PATENT DOCUMENTS

| | | |
|---|---|---|
| EP | 1 195 177 A1 | 4/2002 |
| GB | 2 371 964 A | 8/2002 |

OTHER PUBLICATIONS

Graham P.A., et al.,, "Dynamic Surface Matching for Patient Positioning in Radiotherapy," Information Visualization, Jul. 29, 1998, pp. 16–24, XP010292559.

"Highly Oriented Pyrolytic Graphite", download from http://www.win.ne.jp/~techno/e HOPG.html on Jul. 29, 2002. 1pg.

"Overview of Cancer and Radiation Therapy", download from http://www.vetradtherapy.com/overview.html on Jul. 24, 2002. 6pgs.

* cited by examiner

Primary Examiner—Allen C. Ho

(57) ABSTRACT

A system includes presentation of a view of portions of structures that would be intercepted by a path of radiation during radiation treatment from a perspective of a location. The radiation enters an entry surface of a radiation-focusing lens, exits an exit surface of the radiation-focusing lens, and is substantially focused on a focal area. The location is located such that a plane perpendicular to an axis of the path, intercepting the exit surface, and positioned between the entry surface and the focal area would be located between the location and the lens.

15 Claims, 8 Drawing Sheets

SYSTEM TO PRESENT FOCUSED RADIATION TREATMENT AREA

CROSS-REFERENCE TO RELATED APPLICATIONS

This application claims priority to U.S. Provisional Application No. 60/377,352, filed May 1, 2002 and entitled "System and Method of Focused Orthovoltage Technology for Radiotherapy".

BACKGROUND

1. Field

The present invention relates generally to medical treatment using focused radiation, and more particularly to planning and/or verification systems used in conjunction with such treatment.

2. Description

Conventional radiation treatment typically involves directing a radiation beam at a tumor located within a patient. The radiation beam is intended to deliver a predetermined dose of treatment radiation to the tumor according to an established treatment plan. The goal of such treatment is to kill tumor cells through ionizations caused by the radiation.

Healthy tissue and organs are often in the treatment path of the radiation beam during radiation treatment. The healthy tissue and organs must be taken into account when delivering a dose of radiation to the tumor, thereby complicating determination of the treatment plan. Specifically, the plan must strike a balance between the need to minimize damage to healthy tissue and organs and the need to ensure that the tumor receives an adequately high dose of radiation. In this regard, cure rates for many tumors are a sensitive function of the radiation dose they receive.

It is therefore necessary to design treatment plans to maximize radiation delivered to a target while minimizing radiation delivered to healthy tissue. Even if such a plan is designed, the goals of maximizing target radiation and minimizing healthy tissue radiation may not be achieved if the radiation is not delivered exactly as required by the treatment plan. More specifically, poor treatment planning and errors in radiation delivery can each result in low irradiation of tumors and high irradiation of sensitive healthy tissue.

In conventional radiation treatment systems, a linear accelerator generates a divergent beam of photons having energies in excess of 1 MeV and the beam is directed toward a treatment area of a patient. The beam may be shaped by beam shaping devices before reaching the treatment area in an attempt to ensure that beam shape closely matches the shape of the treatment area and does not harm healthy tissue. Accordingly, conventional megavoltage treatment is planned by considering the divergence of the beam, the distance over which the beam travels to the treatment area, and known data representing organs and other structures internal to the patient.

A kilovoltage radiation treatment system such as those described in U.S. Pat. No. 6,366,801 to Cash et al produces a divergent beam of traditional medical x-rays having energies in the 50 to 150 keV range and focuses the beam on a target using a lens designed for this purpose. Since the beam follows a path that is quite different from the path followed by megavoltage treatment beams, the above-described conventional systems are not suitable for planning and verification of kilovoltage radiation treatment. It would therefore be beneficial to provide a system for planning and verification of radiation treatment that efficiently accounts for the path of a focused treatment beam.

SUMMARY

To address at least the above problems, some embodiments of the present invention provide a system, method, apparatus, and means to determine a path of radiation, the radiation to enter an entry surface of a radiation-focusing lens, to exit an exit surface of the radiation-focusing lens and substantially focused on a focal area, to determine portions of structures that would be intercepted by the path during radiation treatment, and to present a view of the intercepted portions from a perspective of a location. The location is located such that a plane perpendicular to an axis of the path, intercepting the exit surface, and positioned between the entry surface and the focal area would be located between the location and the lens.

In other aspects, a system is provided having a first device that includes a radiation source for emitting radiation and a radiation-focusing lens for substantially focusing the radiation on a focal area, the radiation entering an entry surface of the lens and exiting an exit surface of the lens. The system further includes a processor for determining a path of the radiation and for determining portions of internal structures of a patient that would be intercepted by the path during radiation treatment, and a display for presenting a view of the intercepted portions from a perspective of a location. The location is located such that a plane perpendicular to an axis of the path, intercepting the exit surface, and positioned between the entry surface and the focal area would be located between the location and the lens. In a further aspect, the system includes a second device for acquiring data representing the internal structures of the patient, wherein the processor determines the portions of internal structures of the patient that would be intercepted by the path based at least on the data representing the internal structures of the patient.

In still other aspects, a view of portions of structures that would be intercepted by a path of radiation during radiation treatment is presented from a perspective of a location, the radiation to enter an entry surface of a radiation focusing lens, to exit an exit surface of the radiation-focusing lens and to be substantially focused on a focal area. The location is located such that a plane perpendicular to an axis of the path, intercepting the exit surface, and positioned between the entry surface and the focal area would be located between the location and the lens.

The present invention is not limited to the disclosed embodiments, however, as those of ordinary skill in the art can readily adapt the teachings of the present invention to create other embodiments and applications.

BRIEF DESCRIPTION OF THE DRAWINGS

The exact nature of this invention, as well as its objects and advantages, will become readily apparent from consideration of the following specification as illustrated in the accompanying drawings, in which like reference numerals designate like parts, and wherein.

DETAILED DESCRIPTION

The following description is provided to enable any person of ordinary skill in the art to make and use the invention and sets forth the best modes contemplated by the inventor for carrying out the invention. Various modifications, however, will remain readily apparent to those in the art.

Figure 1:
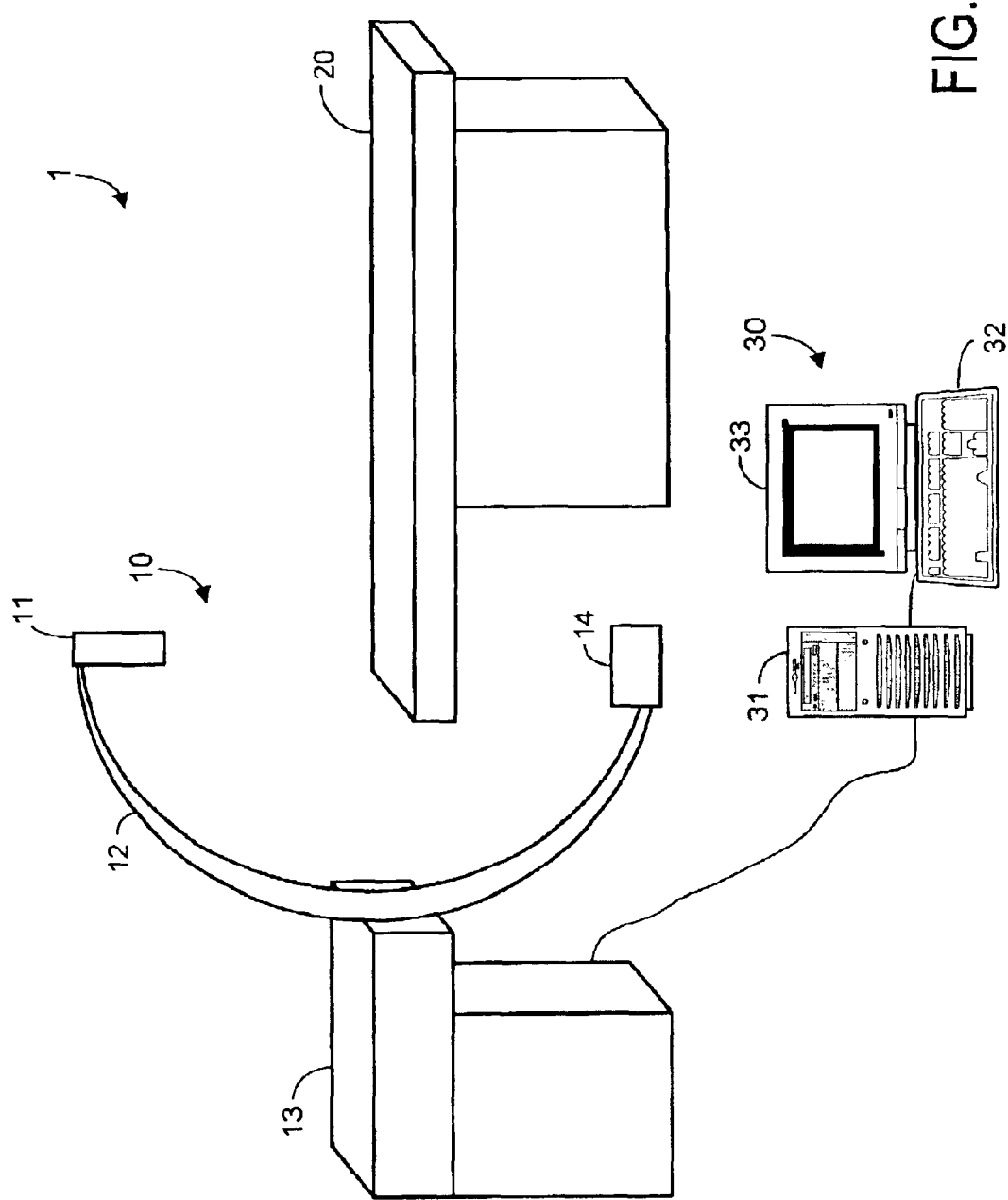
FIG. 1 is a diagram illustrating a radiation treatment room according to some embodiments of the present invention.

FIG. 1 illustrates radiation treatment room 1 pursuant to some embodiments of the present invention. Radiation treatment room 1 includes kilovoltage radiation treatment unit 10, treatment table 20 and operator station 30. The elements of radiation treatment room 1 are used to deliver kilovoltage radiation to a patient according to a treatment plan. In this regard, kilovoltage radiation refers herein to any radiation having energies ranging from 50 to 150 keV. However, it should be noted that some embodiments of the present invention may be used in conjunction with any focused radiation beam.

Treatment unit 10 is used to deliver treatment radiation to a treatment area and includes treatment head 11, c-arm 12, base 13 and imaging system 14. Treatment head 11 includes a beam-emitting device such as an x-ray tube for emitting kilovoltage radiation used during calibration and/or treatment. The radiation may comprise electron, photon or any other type of radiation. Treatment head 11 also includes a cylinder in which are disposed optics such as a focusing lens for optically processing the emitted radiation. Treatment head 11 will be described in more detail below with respect to FIG. 2.

C-arm 12 is slidably mounted on base 13 and can therefore be moved in order to change the position of treatment head 11 with respect to table 20. In some embodiments, base 13 also includes a high-voltage generator for supplying power used by treatment head 11 to generate kilovoltage radiation. Many c-arm/base configurations may be used in conjunction with some embodiments of the present invention, including configurations in which base 13 is rotatably mounted to a ceiling of room 1, configurations in which one c-arm is slidably mounted on another c-arm, and configurations incorporating multiple independent c-arms.

Examples of c-arm kilovoltage radiation units include Siemens SIREMOBIL™, MULTISTAR™, BICOR™ and POLYSTAR™ units as well as other units designed to perform tomography and/or angiography. These units are often less bulky and less costly than megavoltage radiation systems. Of course, any system for delivering a focused radiation beam may be used in conjunction with some embodiments of the present invention.

Imaging system 14 produces an image based on the radiation emitted by treatment head 11. The appearance of the image depends upon the attenuative properties of objects located between treatment head 11 and imaging system 14 while the radiation is emitted. Imaging system 14 may comprise an image intensifier and a camera. An image intensifier is a vacuum tube that converts X-rays to visible light, which is then detected by the camera to produce an image. Imaging system 14 may also comprise a flat-panel imaging system that uses a scintillator and silicon elements to produce an image based on received radiation.

A patient is placed on treatment table 20 during treatment in order to position an area of interest between treatment head 11 and imaging system 14. Accordingly, table 20 may comprise mechanical systems for moving itself with respect to unit 10.

Operator station 30 includes a processor 31 in communication with an input device such as keyboard 32 and an operator display 33. Operator station 30 is typically operated by an operator who administers actual delivery of radiation treatment as prescribed by an oncologist. Operator station 30 may be located apart from treatment unit 10, such as in a different room, in order to protect the operator from radiation. It should be noted, however, that kilovoltage radiation treatment does not require protective measures to the extent of those taken during megavoltage radiation therapy, resulting in less costly therapy.

Processor 31 may store processor-executable process steps according to some embodiments of the present invention. In some aspects, the process steps are executed by operator station 30, treatment unit 10, imaging system 14, and/or another device to determine a path of radiation, the radiation to enter an entry surface of a radiation-focusing lens, to exit an exit surface of the radiation-focusing lens and substantially focused on a focal area, to determine portions of structures that would be intercepted by the path during radiation treatment, and to present a view of the intercepted portions from a perspective of a location.

The process steps may also be executed to present a view of portions of structures that would be intercepted by a path of radiation during radiation treatment from a perspective of a location, the radiation to enter an entry surface of a radiation focusing lens, to exit an exit surface of the radiation-focusing lens and to be substantially focused on a focal area. The location is located such that a plane perpendicular to an axis of the path, intercepting the exit surface, and positioned between the entry surface and the focal area would be located between the location and the lens. The view may be presented on operator display 33.

The above-described steps may also be embodied, in whole or in part, by hardware of processor 31, treatment unit 10, imaging system 14, and another device. Of course, each of the devices shown in FIG. 1 may include less or more elements than those shown. In addition, embodiments of the invention are not limited to the devices shown.

Figure 2:
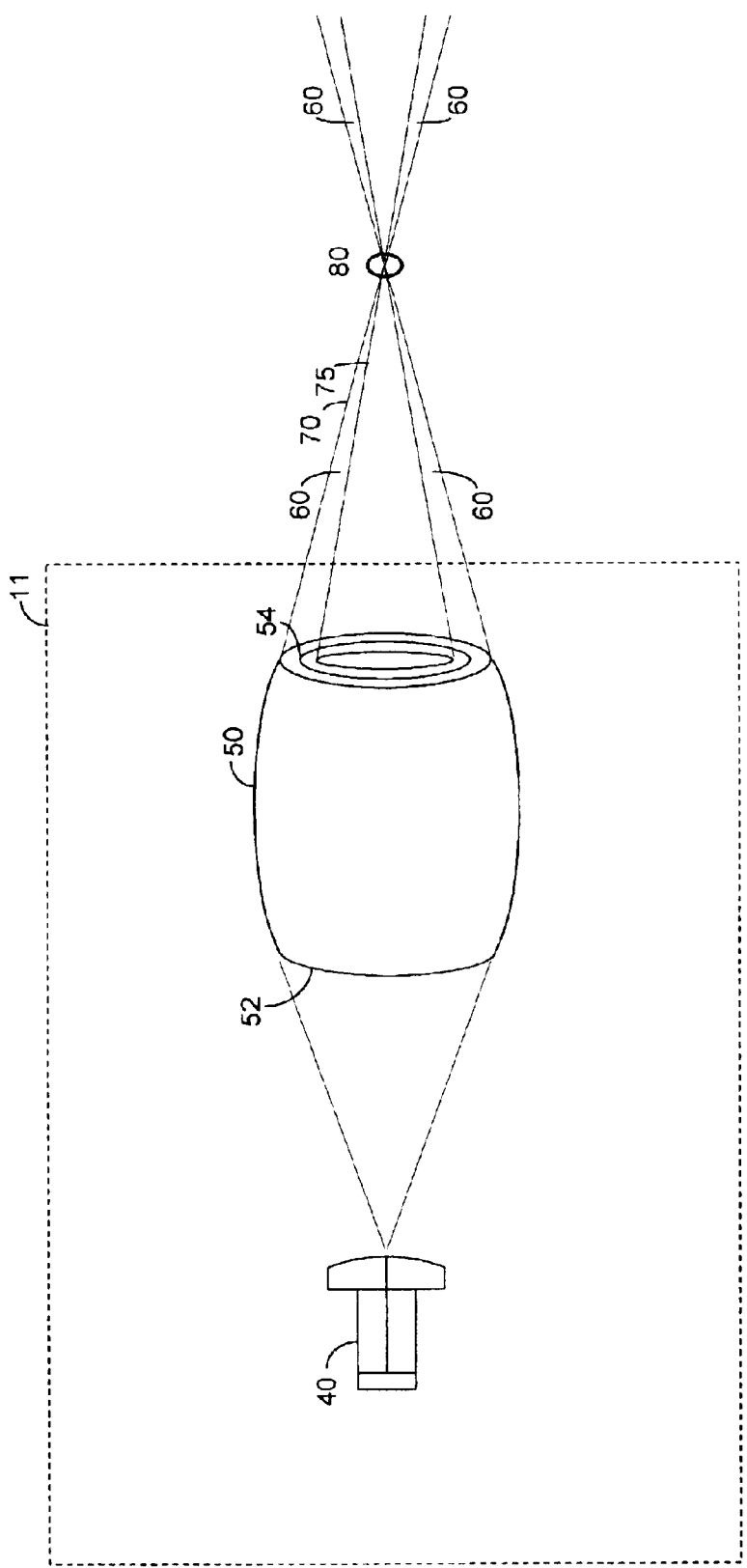
FIG. 2 is a diagram illustrating a radiation-focusing lens according to some embodiments of the present invention.

FIG. 2 is a representative view of elements of treatment head 11 according to some embodiments of the present invention. As shown, treatment head 11 includes x-ray tube 40 and lens 50. In operation, radiation is emitted by x-ray tube 40 toward lens 50. The radiation enters entry surface 52 of lens 50 and some or all of the radiation exits exit surface 54.

Lens 50 may comprise any radiation-focusing lens, including those having a shape different from that illustrated. In this regard, lens 50 of FIG. 2 comprises thin strips of reflective material arranged in the form of several barrels nested around a central axis. Each "barrel" is separated from adjacent "barrels" by plexiglass or another optically neutral substrate.

In some embodiments of lens 50, different points along lens 50 act as focusing elements. The path the x-ray follows for each point on the lens is slightly different. Hence, the conical shape of path 60 is not due to the barrel shape of lens 50 but to the paths of each x-ray hitting a different location on planes perpendicular to path 60 but not at focal area 80.

Lens 50 may also comprise any other radiation-focusing lenses such as those described in U.S. Pat. No. 6,359,963 to Cash, in U.S. Pat. No. 5,604,782 to Cash, Jr., in U.S. Patent Application Publication No. 2001/0043667 of Antonell et al., and/or elsewhere in currently or hereafter-known art.

Highly Oriented Pyrolitic Graphite (HOPG) may be used as the reflective material of lens 50. HOPG consists of planes of carbon atoms that are highly oriented toward one another. In the ideal variant, these planes are parallel to one another.

By virtue of its composition, shape and construction and of properties of the emitted radiation, lens 50 directs the radiation along path 60. Geometrically, path 60 comprises the hollow conical volume between outer cone surface 70 and inner cone surface 75.

Lens 50 operates to substantially focus all or a portion of the radiation on focal area 80. Focal area 80 may be a point in space or a larger area. In some embodiments of lens 50, focal area 80 is approximately 1 cm in diameter. According to the FIG. 2 embodiment, focal area 80 is spaced from an exit surface of lens 50 by a distance determined by the composition, shape and construction of lens 50 as well as by characteristics of the emitted radiation.

Path 60 does not terminate at focal area 80. Rather, path 60 continues thereafter, becoming further attenuated and unfocused as its distance from focal area 80 increases. In some embodiments, the divergence of path 60 from focal area 80 roughly mirrors its convergence thereto.

It should be noted that treatment head 11 may also include beam shaping devices such as one or more jaws, collimators, reticles and apertures. By changing the shape of path 60, these devices may cause a change in the shape and/or position of focal area 80. The devices may be placed between lens 50 and focal area 80 and/or between x-ray tube 40 and lens 50.

Figure 3:
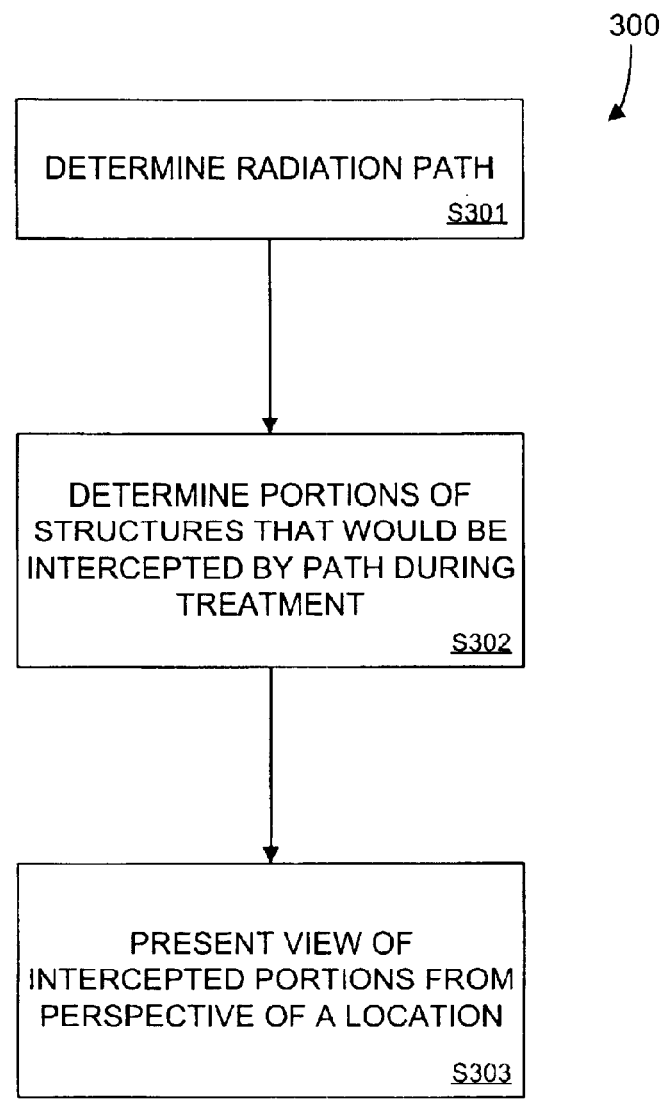
FIG. 3 comprises a flow diagram illustrating process steps according to some embodiments of the present invention.

FIG. 3 comprises a flow diagram of process steps 300 to present a view of potentially-radiated structures according to some embodiments of the invention. Process steps 300 may be embodied by hardware and/or software of processor 31, treatment unit 10; imaging system 14, and/or another device in direct or indirect communication with display 30.

Process steps 300 begin at step S301, in which a radiation path is determined. In this regard, process steps 300 may be executed during the planning of future radiation treatment and therefore the determined radiation path may be a path followed by planned, rather than actual, radiation. As shown in FIG. 2, the path may be a path of radiation planned to enter an entry surface of a radiation-focusing lens, to exit an exit surface of the lens, and to be substantially focused on a focal area.

In the present example, the determined path of radiation is path 60 of radiation exiting exit surface 54. Path 60 includes areas lying between focal area 80 and lens 50 as well as areas located farther from lens 50 than focal area 80. Path 60 may be determined based on an energy and type of radiation to be transmitted by tube 40, characteristics of lens 50 and other factors known in the art. According to some embodiments, path 60 is determined by performing ray tracing from a location of focal area 80 to exit surface 54. In some embodiments, a size and location of path 60 with respect to lens 50 is determined in step S301.

Figure 4:
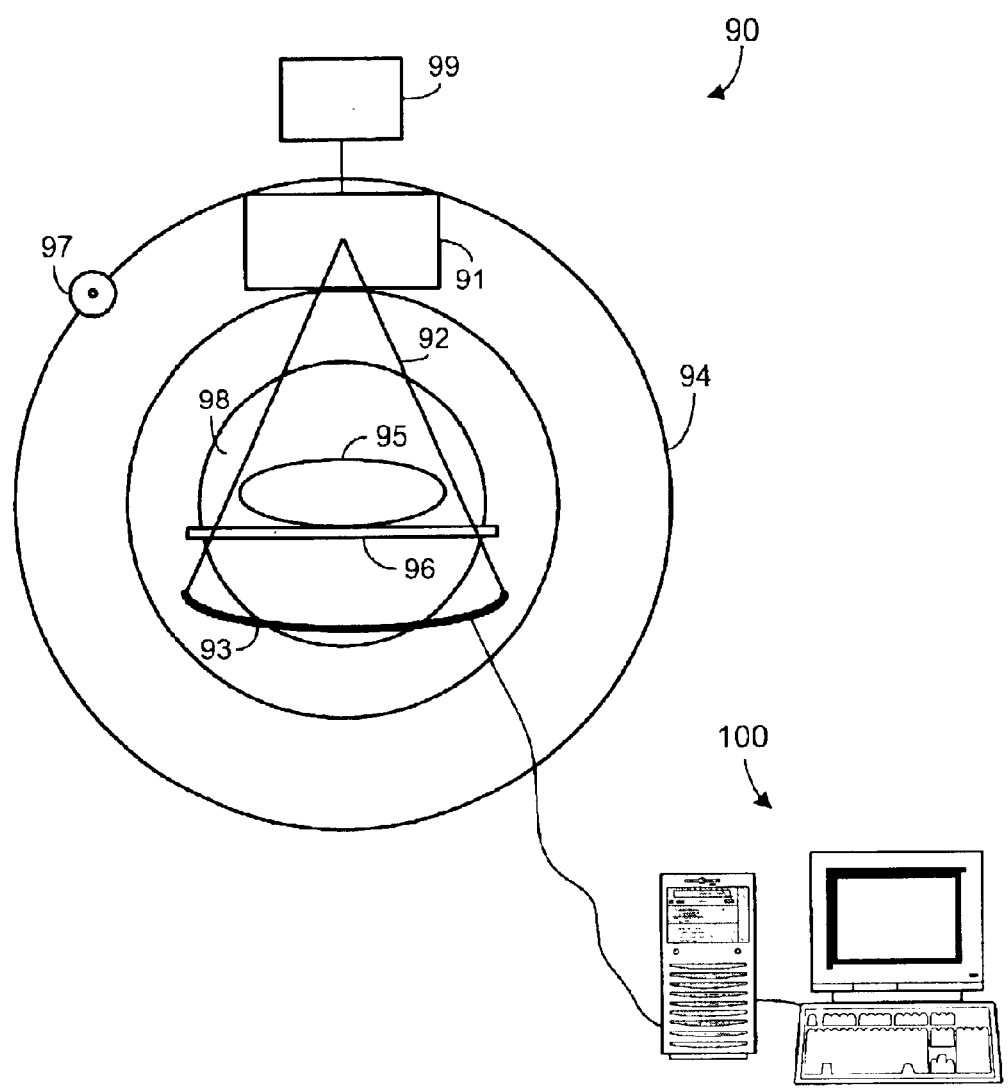
FIG. 4 is a view of a diagnostic computed tomography (CT) device.

Next, in step S302, portions of structures that would be intercepted by the path during treatment are determined. In some embodiments, this determination is based on data representing structures internal to a patient. This data may be obtained prior to step S302 using a computed tomography (CT) scanner, such as CT scanner 90 of FIG. 4.

CT scanner 90 includes x-ray source 91 for emitting fan-shaped x-ray beam 92 toward radiation receiver 93. Both x-ray source 91 and radiation receiver 93 are mounted on ring 94 such that they may be rotated through 360 degrees while maintaining the physical relationship therebetween. In order to acquire data representing structures internal to a patient (i.e., CT data), patient 95 lies on patient bed 96. Next, x-ray source 91 and receiver 93 are rotated by rotation drive 97 around a measurement field 98 in which patient 94 lies.

During this rotation, x-ray source 91 is powered by high-voltage generator 99 to transmit radiation toward receiver 93. At predetermined rotational angle positions, receiver 93 produces sets of data and the sets of data are transmitted to computer system 100. Computer system 100 calculates attenuation coefficients of predetermined image points from the registered data sets to generate data representing internal structures of patient 95.

Figure 5:
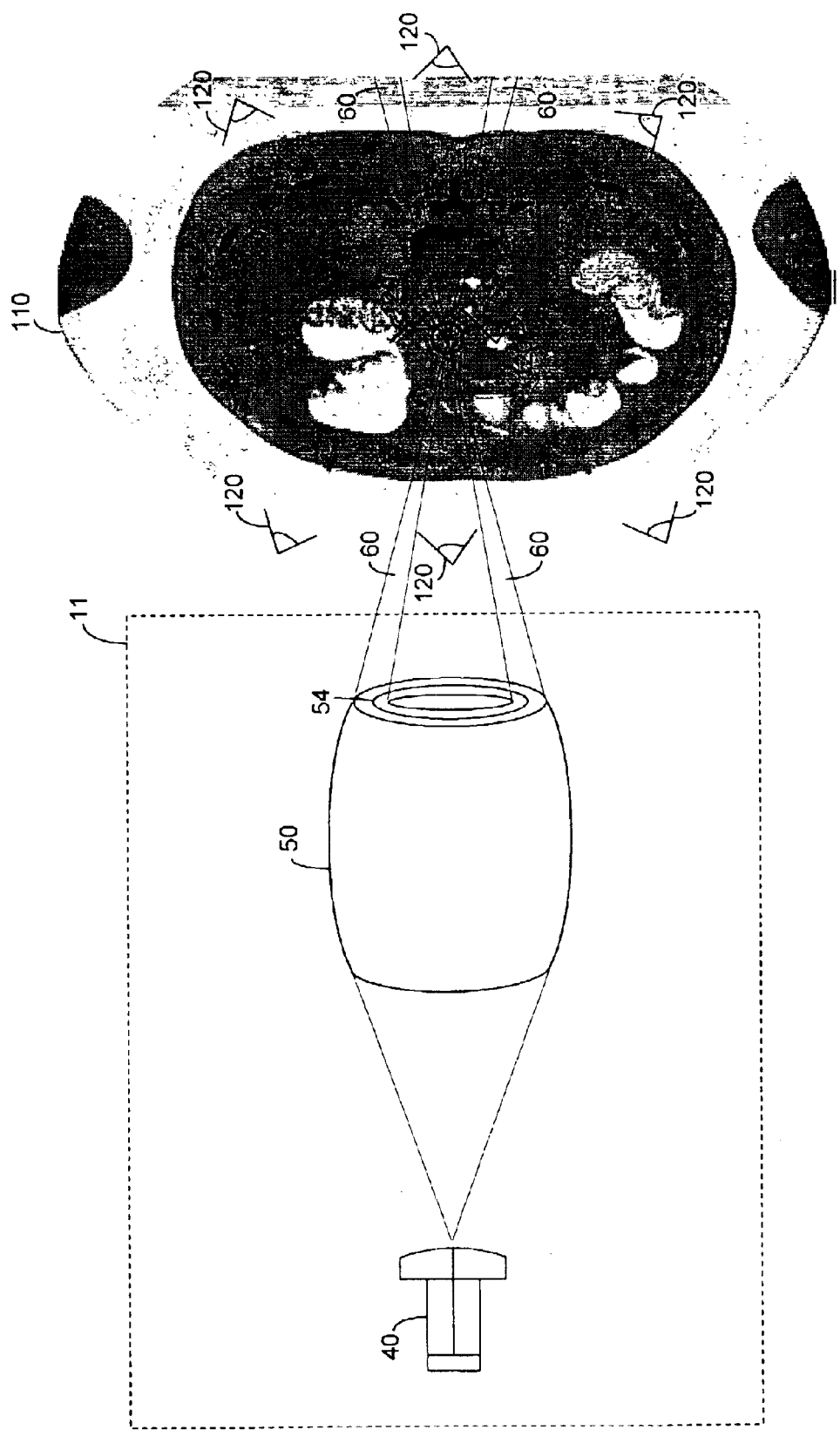
FIG. 5 is a diagram illustrating radiation treatment planning according to some embodiments of the present invention.

FIG. 5 illustrates treatment planning for the purposes of the step S302 determination according to some embodiments. CT slice 110 illustrates a two-dimensional view of portions of a patient's internal structures. CT slice 110 may be generated using CT scanner 90 as described above. In particular, CT slice 110 represents structures within a patient that intercept a plane passing through the patient's torso and perpendicular to the patient's spine.

In some embodiments, processor 31 uses data of CT slice 110 and the path determined in step S301 to determine an intersection of the two sets of data. This determination may proceed by assuming that focal area 80 is located at a target location within CT data 110 and by determining an intersection of path 60 converging on focal area 80 with the data of CT slice 110. Of course, step S302 may also comprise determining an intersection of path 60 with a set of CT data representing a three-dimensional volume within a patient.

Next, in step S303, a view of the determined portions is presented from the perspective of a location. According to some embodiments, the location may be any location designated by eyes 120 of FIG. 5. Generally, eyes 120 are shown at locations which are located such that a plane perpendicular to an axis of path 60, intercepting exit surface 54, and positioned between entry surface 52 and focal area 80 would be located between the location and lens 50. More particularly, the location may be at focal area 80, on an axis of path 60, between lens 50 and the intercepted portions, between lens 50 and focal area 80, facing toward lens 50, and/or facing away from lens 50. In this regard, an element or location described herein as being "between" two other elements or locations is only required to lie within a space bounded by two parallel planes, wherein each of the planes includes a respective one of the two other elements or locations and is perpendicular to a line connecting the two other elements or locations.

Figure 6:
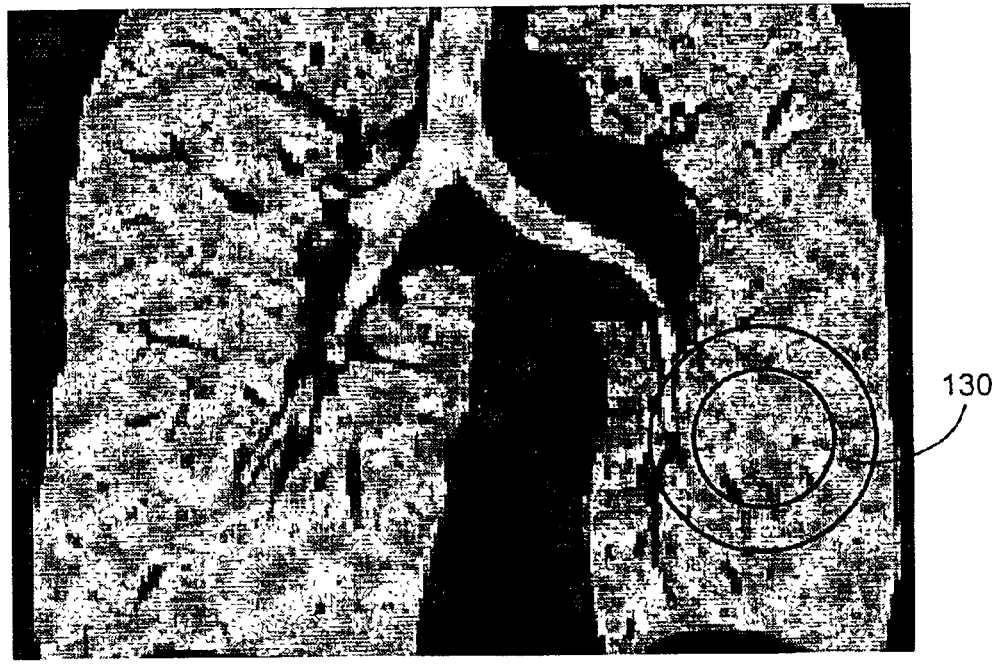
FIG. 6 is a view of portions of structures intercepted by a treatment beam according to some embodiments of the present invention.

The view may be presented on display 33 in many forms. For example, the view may comprise an intersection of the intercepted portions, the determined path and a plane. FIG. 6 presents a view from a perspective of focal area 80 looking toward lens 50 according to some embodiments of the invention. As shown, annular disk 130 indicates an intersection of intercepted internal portions, path 60, and a plane passing through the length of a patient. It should be noted that a diameter of annular disk 130 would increase as the plane moves closer to lens 50 due to the convergence of path 60 on focal area 80. It should also be noted that disk 130 may appear elliptical if the perspective location was not on an axis of path 60 and/or if the plane was not perpendicular to the axis.

Figure 7:
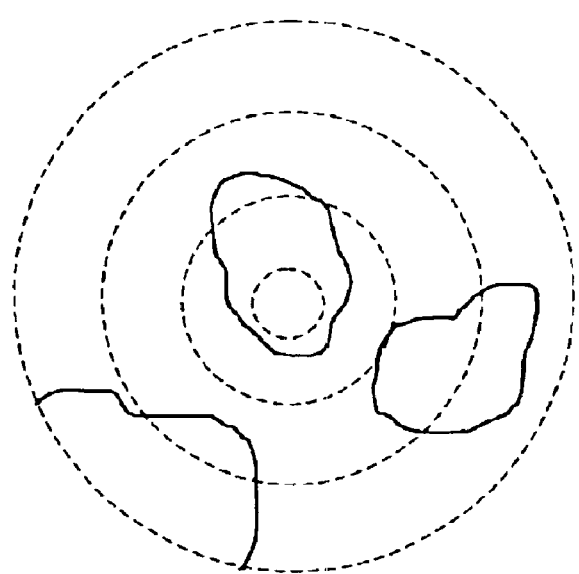
FIG. 7 is a view of portions of structures intercepted by a treatment beam according to some embodiments of the present invention.

FIG. 7 comprises a view of portions determined in step S302 according to some embodiments. In particular, the view comprises a projection of one or more intercepted portions onto a plane perpendicular to the axis of path 60, not intersecting internal areas of the subject patient, and normal to a surface of the patient. Such a view presents information relating to volumes of internal structures to be irradiated. In particular, each depicted ring corresponds to a particular dose and includes internal portions intercepted by path 60 at a given plane corresponding to the ring size. Accordingly, the FIG. 7 view is based on a combination of the rings shown in FIG. 6. In some embodiments, the portions shown within each ring are colored according to their respective absorbed dosages.

Figure 8:
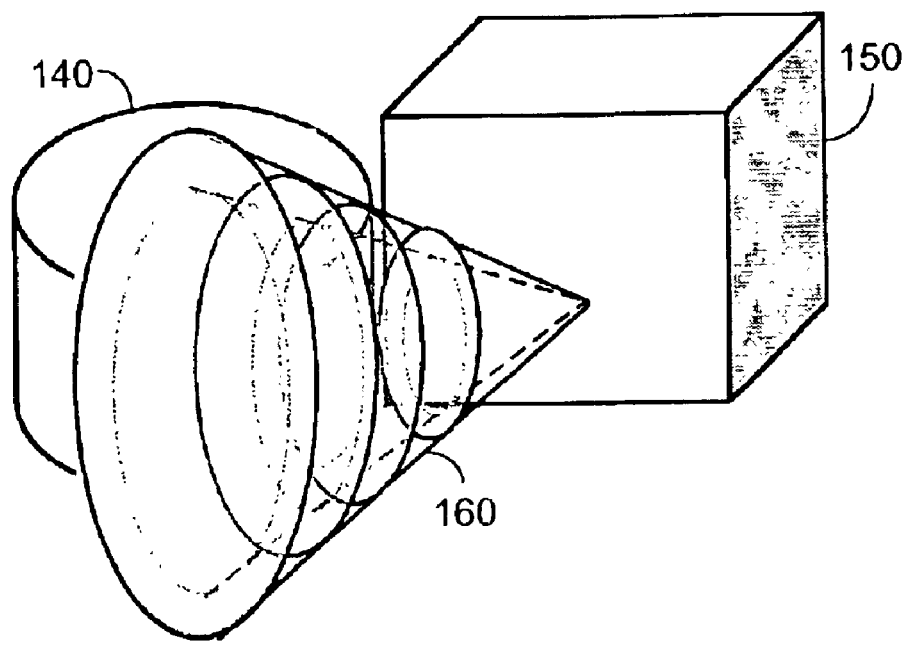
FIG. 8 is a view of portions of structures intercepted by a treatment beam according to some embodiments of the present invention.

The view presented in step S303 may also comprise a three-dimensional view showing three-dimensional representations of internal portions of a patient in conjunction with a three-dimensional representation of path 60. FIG. 8 is one embodiment of such a view, and allows efficient visualization of intercepted portions of internal patient structures. In this regard, cylinder 140 and cube 150 represent organs, the solid lines of cone 160 represent outer surface 70 of path 60, and the dashed lines represent inner surface 75 of path 60.

The intercepted portions may be represented differently than as shown in FIGS. 6 through 8. For example, the portions may be color-coded based on an amount of radiation to be respectively received using known image processing techniques. In addition, the view may include only the intercepted portions and no internal portions that would not be intercepted by the radiation path. Several views may be presented in rapid succession, allowing an operator to "fly through" irradiated portions of internal structures.

Views according to embodiments of the present invention may be used to plan radiation treatment. For example, a view may be used to present portions of internal structures that would be intercepted by radiation during planned radiation treatment. Based on the view, an oncologist may or may not alter the planned treatment. A view according to some embodiments of the present invention may also be used to verify an impending treatment. In such an instance, a patient may be placed on table 20 and CT data representing the patient may be generated. Portions of structures to be irradiated are then determined based on the CT data, the radiation path, and a distance between the radiation-focusing lens and the patient. A view of these portions may be used to reposition the patient with respect to the treatment head and/or to change characteristics of the radiation to be delivered.

Those in the art will appreciate that various adaptations and modifications of the above-described embodiments can be configured without departing from the scope and spirit of the invention. Therefore, it is to be understood that, within the scope of the appended claims, the invention may be practiced other than as specifically described herein.

What is claimed is:

1. A method comprising:

determining a path of x-ray radiation, the x-ray radiation to enter an entry surface of an x-ray radiation-focusing lens, to exit an exit surface of the x-ray radiation-focusing lens and to be substantially focused on a focal area;

determining portions of structures that would be intercepted by the path during x-ray radiation treatment; and presenting a view of the intercepted portions from a perspective of a location, wherein the location is located such that a plane perpendicular to an axis of the path and intercepting the exit surface would be located between the location and the entry surface.

2. A method according to claim 1, wherein the view comprises a projection of the intercepted portions onto a second plane.

3. A method according to claim 1, wherein the view comprises a three-dimensional view of portions intercepted by a three-dimensional portion of the path.

4. A method according to claim 1, wherein the view comprises an intersection of the portions, the path and a second plane.

5. A method according to claim 1, wherein the location comprises the focal area.

6. A method according to claim 1, wherein the focal area is between the location and the exit surface.

7. A method according to claim 1, wherein the location intercepts the axis.

8. A method according to claim 1, wherein the view comprises an indication of an amount of x-ray radiation to be received by one or more of the intercepted portions.

9. A method according to claim 8, wherein the one or more intercepted portions are color-coded based on the amount of x-ray radiation to be received.

10. A method according to claim 1, wherein the focal area is located between the lens and the portions.

11. A method according to claim 1, wherein the portions are located between the lens and the focal area.

12. A computer-readable medium storing computer-executable process steps, the process steps comprising:

a step to determine a path of x-ray radiation, the x-ray radiation to enter an entry surface of an x-ray radiation focusing lens, to exit an exit surface of the x-ray radiation-focusing lens and to be substantially focused on a focal area;

a step to determine portions of structures that would be intercepted by the path during x-ray radiation treatment; and a step to present a view of the intercepted portions from a perspective of a location, wherein the location is located such that a plane perpendicular to an axis of the path and intercepting the exit surface would be located between the location and the entry surface.

13. An apparatus comprising:

a memory storing processor-executable process steps;

a processor in communication with the memory and operative in conjunction with the stored process steps to:

determine a path of x-ray radiation, the x-ray radiation to enter an entry surface of an x-ray radiation focusing lens, to exit an exit surface of the x-ray radiation-focusing lens and to be substantially focused on a focal area;

determine portions of structures that would be intercepted by the path during x-ray radiation treatment; and present a view of the intercepted portions from a perspective of a location, wherein the location is located such that a plane perpendicular to an axis of the path and intercepting the exit surface would be located between the location and the entry surface.

14. A system comprising:

a first device comprising:
   an x-ray radiation source for emitting x-ray radiation; and
   an x-ray radiation-focusing lens for substantially focusing the x-ray radiation on a focal area, the x-ray radiation entering an entry surface of the lens and exiting an exit surface of the lens;

a processor for determining a path of the x-ray radiation, the x-ray radiation to enter the entry surface of the x-ray radiation-focusing lens, to exit the exit surface of the x-ray radiation-focusing lens and to be substantially focused on the focal area, and for determining portions of internal structures of a patient that would be intercepted by the path during x-ray radiation treatment; and a display for presenting a view of the intercepted portions from a perspective of a location, wherein the location is located such that a plane perpendicular to an axis of the path and intercepting the exit surface would be located between the location and the entry surface.

15. A system according to claim 14, further comprising:

a second device for acquiring data representing the internal structures of the patient, wherein the processor determines the portions of internal structures of the patient that would be intercepted by the path based at least on the data representing the internal structures of the patient.

* * * * *